(12) United States Patent
Oakey

(10) Patent No.: US 6,584,803 B2
(45) Date of Patent: Jul. 1, 2003

(54) NITROGEN REJECTION METHOD AND APPARATUS

(75) Inventor: John Douglas Oakey, Godalming (GB)

(73) Assignee: The BOC Group plc, Windlesham (GB)

(*) Notice: Subject to any disclaimer, the term of this patent is extended or adjusted under 35 U.S.C. 154(b) by 0 days.

(21) Appl. No.: 10/192,479

(22) Filed: Jul. 10, 2002

(65) Prior Publication Data

US 2003/0019241 A1 Jan. 30, 2003

(30) Foreign Application Priority Data

Jul. 11, 2001 (GB) .............................. 0116960

(51) Int. Cl.⁷ ................................ F25J 3/00
(52) U.S. Cl. .............................. 62/621; 62/628; 62/927
(58) Field of Search ........................... 62/621, 628, 927

(56) References Cited

U.S. PATENT DOCUMENTS

| | | | |
|---|---|---|---|
| 4,415,345 A | 11/1983 | Swallow | |
| 4,588,427 A | 5/1986 | Yao et al. | |
| 4,690,702 A | 9/1987 | Paradowski et al. | |
| 5,257,505 A | * 11/1993 | Butts | ............................ 62/927 |
| 5,339,641 A | * 8/1994 | Mathis et al. | .................. 62/927 |
| 5,421,165 A | 6/1995 | Paradowski et al. | |

OTHER PUBLICATIONS

"Cryogenic Techniques in Enhanced Recovery of Oil and Gas", by Ruhemann, R., *Indian J. Cryog.*, vol. 9, No. 4, pp. 256–261 (1984).

"Wyoming's Shute Creek Plant Uses NRU Unit", by Pruitt et al., *Oil and Gas Journal*, pp. 78–82, Oct. 9, 1989.

"Plant Design Integrates NGL Recovery N2 Rejection", by Davis et al., *Oil and Gas Journal*, pp. 33–39, Nov. 6, 1989.

"Process and Facility with Particularly High Availability", *Kenneth Mason Publications*, Research Disclosure, No. 397, XP–000726402, pp. 276–279, May 1, 1997.

* cited by examiner

*Primary Examiner*—Ronald Capossela
(74) *Attorney, Agent, or Firm*—Philip H. Von Neida; Salvatore P. Pace

(57) ABSTRACT

Nitrogen is rejected from a feed gas stream comprising methane and nitrogen so as to form a methane product. The feed gas stream is cooled in a main heat exchanger and rectified in a double rectification column comprising a higher pressure column, a lower pressure column and a condenser-reboiler placing the higher and lower pressure rectification columns in heat exchange relationship with each other. At least part of the feed gas stream is expanded through a valve into the higher pressure rectification column and the feed gas stream is partially liquefied upstream of the double rectification column. Over a period of time, the mole fraction of nitrogen in the feed gas stream may increase. The operating pressure of the lower pressure rectification column is periodically increased in response to increases in the mole fraction of nitrogen. A back pressure valve may be periodically adjusted to effect the increase in pressure.

12 Claims, 1 Drawing Sheet

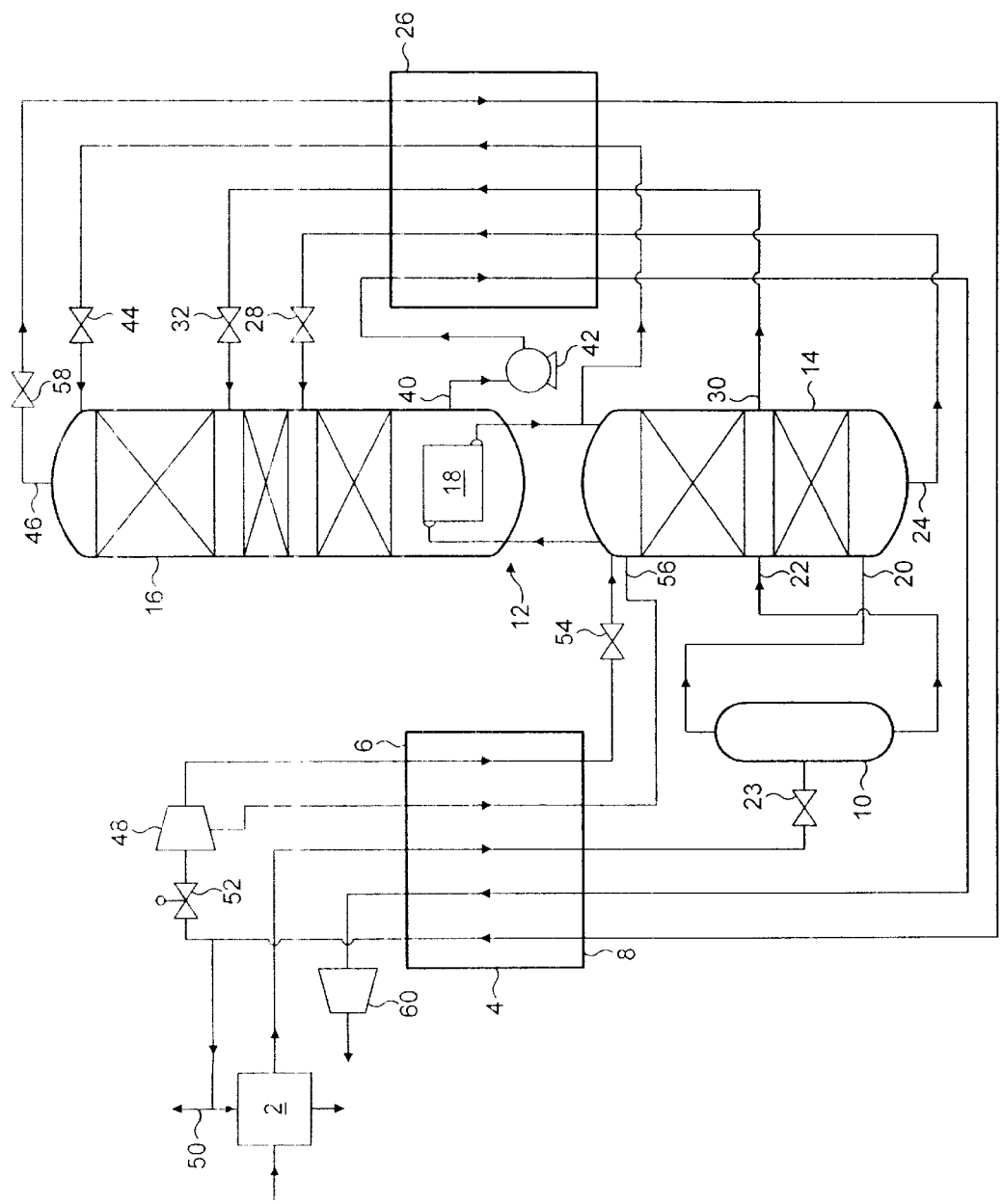

NITROGEN REJECTION METHOD AND APPARATUS

FIELD OF THE INVENTION

This invention relates to a method of and apparatus for rejecting nitrogen from a feed gas stream comprising methane and nitrogen so as to form a methane product.

BACKGROUND OF THE INVENTION

It is known to extract natural gas from underground reservoirs. The natural gas often contains nitrogen. The nitrogen may be in part or totally derived from nitrogen which has been injected into the reservoir as part of an enhanced oil recovery (EOR) or enhanced gas recovery (EGR) operation. A feature of such operations is that the concentration of nitrogen in the natural gas tends to increase with the passage of time from about 5% by volume to about 60% by volume.

U.S. Pat. No. 4,415,345 discloses a process for rejecting the nitrogen from the methane in a double rectification column operating at cryogenic temperatures. A double rectification column comprises a higher pressure rectification column, a lower pressure rectification column, and a condenser-reboiler placing the top of the higher pressure rectification column in indirect heat exchange relationship with a region, usually the bottom, of the lower pressure rectification column. In the process according to U.S. Pat. No. 4,415,345 a stream of a mixture of nitrogen and methane is cooled at elevated pressure to a temperature suitable for its separation by rectification. A part of the feed gas is liquefied. The resulting gas mixture is separated by rectification in a lower pressure rectification column having a condenser-reboiler operatively associated with a bottom region thereof. The reboiling passages of the condenser-reboiler are heated by pressurised nitrogen. Typically, a part of the nitrogen is separated in a higher pressure rectification column and another part flows in a heat pump circuit to and from the top of the lower pressure rectification column. At low nitrogen levels in the feed gas, the higher pressure rectification column is by-passed and all the nitrogen for the condenser-reboiler flows in the heat pump circuit, which is separate from the main heat exchanger used to cool the feed gas stream. As the nitrogen content in the feed gas gradually increases so the higher pressure column is used to provide some of the nitrogen, replacing nitrogen from the heat pump circuit. Eventually, the heat pump circuit is closed and the higher pressure column produces all the nitrogen.

The higher pressure rectification column used in the process according to U.S. Pat. No. 4,415,345 is operated with a second condenser-reboiler at its bottom. As a consequence, there is a high vapour flow therethrough and it needs to be of a relatively large diameter even though it is operated at maximum capacity only at high nitrogen concentrations.

It is an aim of the present invention to provide a method and apparatus that keeps down the vapour traffic through the higher pressure rectification column and thereby makes it possible to keep down the diameter of this column.

SUMMARY OF THE INVENTION

According to the present invention there is provided a method of rejecting nitrogen from a feed gas stream, comprising methane and nitrogen, so as to form a methane product, the mole fraction of nitrogen in the feed gas increasing over a period of time. The method comprises cooling the feed gas stream in a main heat exchanger, rectifying the cooled feed gas stream in a double rectification column comprising a higher pressure rectification column, a lower pressure rectification column, and a condenser-reboiler placing the higher pressure rectification column in heat exchange relationship with the lower pressure rectification column, expanding at least part of the feed gas stream into the higher pressure rectification column, partially liquefying the feed gas stream upstream of the double rectification column, and periodically increasing the operating pressure of the lower pressure rectification column, in response to increases in the mole fraction of nitrogen in the feed gas.

The invention also provides apparatus for rejecting nitrogen from a feed gas stream comprising methane and nitrogen so as to form a methane product. The apparatus comprises a main heat exchanger for cooling the feed gas stream, a double rectification column for rectifying the feed gas stream comprising a higher pressure rectification column, a lower pressure rectification column, and a condenser-reboiler placing the higher pressure rectification column in heat exchange relationship with the lower pressure rectification column, and an expansion device downstream of the main heat exchanger communicating with the higher pressure rectification column, the expansion device being arranged so as, in use, to introduce a part of the feed gas stream into the higher pressure rectification column in liquid state, characterised in that there is a back pressure regulating valve associated with the lower pressure rectification column which is operable to increase the pressure in the lower pressure rectification column As the mole fraction of nitrogen in the feed gas mixture becomes greater with the passage of time, so the flow of product methane becomes less, and so less of the feed gas mixture is liquefied against the redirect flow of the product stream. In consequence, there is a tendency for an ever increasing proportion of the feed gas mixture to enter the higher pressure rectification column in vapour state with the passage of time. Thus, in its normal operating lifetime, which may well exceed ten years or more, and last until the reservoir which is the source of the feed gas mixture is effectively exhausted, the double rectification column may have to cope with a very wide range of vapour loadings, posing considerable design problems.

The obvious solution to these problems would be to arrange for all the feed gas mixture to enter the higher pressure rectification column in vapour state. Therefore, changes in the composition of the feed gas mixture would not substantially affect the vapour loading of the higher pressure rectification column. However, one disadvantage of such a procedure, is that the vapour loading of the higher pressure rectification column would always be at a maximum.

The method and apparatus according to the invention make it possible, however, to reduce the effective range of vapour loadings that both rectification columns have to face during their operating lifetime. This is primarily because increasing the operating pressure of the lower pressure rectification brings about a concomitant increase in the operating pressure of the higher pressure rectification column. Increasing the operating pressure of the higher pressure rectification column enables it to receive more vapour per unit time for operation at a given constant percentage of flood. In addition, increasing the operating pressure of the higher pressure rectification column tends to reduce the proportion of the feed gas mixture that passes out of the expansion device in liquid state. These two factors enable the method and apparatus according to the invention to be operated with a lower range of effective vapour loadings on the higher pressure rectification column than would otherwise be possible.

Preferably, particularly when the mole fraction of nitrogen in the feed gas mixture is less than 0.15, a first flow of gas is passed as a first recycle gas flow from the lower pressure rectification column to the higher pressure rectification column. The first recycle gas flow is compressed, is cooled in the main heat exchanger, is liquefied in a further condenser-reboiler, and is introduced into the higher pressure rectification column. This counteracts a tendency for the double rectification column to be short of reflux when the mole fraction of nitrogen in the feed gas mixture is relatively low, particularly when it is 0.15 or less.

A product methane stream is preferably withdrawn in liquid state from the lower pressure rectification column, is raised in pressure, and is vaporised at least in part in the main heat exchanger. A second recycle gas flow from the lower pressure rectification column is preferably compressed, is cooled in the main heat exchanger, and is introduced at least partly in liquid state into the top of the higher pressure rectification column via a second expansion device. Preferably the second recycle flow is compressed to a higher pressure than the first recycle flow, the higher pressure typically being a supercritical pressure. More preferably, the first and second recycle flows are compressed in the same plural stage compressor, the second recycle flow being taken from a stage of the compressor downstream of the one from which the first recycle flow is taken.

It is, however, possible to use separate compressors for these purposes, or indeed to take all the compressed recycle gas at the same pressure and pass it through the same second expansion device. In this latter arrangement a two phase fluid flow passes out of the second expansion device with the vapour part of the two phase flow constituting the first recycle gas stream and the liquid part of the two phase flow constituting the second recycle flow. All these arrangements make it possible for the temperature—enthalpy profile of the streams being cooled in the main heat exchanger to be kept as close match to the temperature—enthalpy profile of the streams being warmed in the main heat exchanger. As a result the main heat exchanger can be operated at a good thermodynamic efficiency.

The back pressure regulating valve is preferably operably associated with means for changing its setting in response to an increase in the mole fraction of nitrogen in the feed gas mixture. If desired, the control means may make use of an algorithm relating the optimum operating pressure of the lower pressure rectification column to the mole fraction of nitrogen in the feed gas mixture. Alternatively, and more preferably, the pressure regulating valve may be controlled so as to maintain a constant percentage recovery of methane in the product gas.

Preferably, a vent stream is taken from the first recycle gas flow upstream of its compression and is vented from the method and apparatus according to the invention.

Preferably, there is a flow control valve operable to control the size of the first recycle flow.

The pressurised liquid product methane stream is preferably warmed, without being vaporised, in a further heat exchanger upstream of its vaporisation in the main heat exchanger.

Preferably, all the bottom fraction obtained in the higher pressure rectification column is withdrawn therefrom and is sent to the lower pressure rectification column. There is therefore no reboiling of this fraction in the higher pressure rectification column.

BRIEF DESCRIPTION OF THE DRAWING

The method according to the invention will now be described by way of example with reference to the accompanying drawing which is a schematic flow diagram of a nitrogen rejection plant.

The drawing is not to scale.

DETAILED DESCRIPTION OF THE INVENTION

A stream of natural gas or gaseous nitrogen-methane mixture is recovered by known means not forming part of this invention from an underground oil or gas reservoir. The stream is typically recovered at a pressure in the order of 40 bar absolute. The stream may be subjected to preliminary treatment (not shown) in order to remove any hydrogen sulphide or other sulphur-containing impurity therefrom. Such purification of natural gas is well known in the art and need not be referred to in further detail herein. After removal of any such hydrogen sulphide impurity, the elevated pressure methane-nitrogen stream still typically contains water vapour impurity. The water vapour is removed by passage through a purification unit 2. The purification unit 2 preferably comprises a plurality of adsorption vessels containing adsorbent able selectively to adsorb water vapour from the feed gas stream. Such purification units typically operate on a pressure swing adsorption or a temperature swing adsorption cycle, the latter generally being preferred. If the feed gas stream also contains carbon dioxide impurity, the purification unit can additionally contain an adsorbent selected for carbon dioxide so as to effect the carbon dioxide removal.

The resulting purified feed gas stream now consisting essentially of nitrogen and methane flows through a main heat exchanger 4 from its warm end 6 to its cold end 8. The main heat exchanger 4 comprises a plurality of heat exchange blocks preferably joined together to form a single unit. Downstream of the main heat exchanger 4, the feed gas stream is expanded through a throttling valve 23 into a phase separator 10. Depending on its pressure, the feed gas stream either becomes liquid in the main heat exchanger 4 or on expansion through the throttling valve 23. Typically, depending on its composition, at least 75 mole percent of the feed gas stream is liquefied. In consequence, the vapour flow is reduced, thus making possible the use of a smaller diameter higher pressure rectification column than would otherwise be required. The vapour is disengaged from the liquid in the phase separator 10. A stream of the vapour phase flows from the top of the phase separator 10 through an inlet 20 into the bottom region of a higher pressure rectification column 14 forming part of a double rectification column 12 with a lower pressure rectification column 16 and a condenser-reboiler 18 thermally linking the top of the higher pressure rectification column 14 to the bottom of the lower pressure rectification column 16. A stream of the liquid phase flows from the bottom of the phase separator 10 into an intermediate mass exchange region of the higher pressure rectification column 14 through another inlet 22.

Typically the feed gas stream enters and leaves the purification unit 2 at a pressure well in excess of the operating pressure of the higher pressure rectification column 14. As a result, refrigeration for the plant is created by passage of the feed stream through the throttling valve 23 with the cold thus operated being given up to incoming streams. This refrigeration meets most of the refrigeration requirements of the method according to the invention and as a result there is typically no need to supply any turbo-expander for this purpose.

The feed gas mixture is separated in the higher pressure rectification column 14 into a vaporous nitrogen top fraction and a liquid methane-enriched bottom fraction. A stream of the methane-enriched bottom fraction is withdrawn from the higher pressure rectification column 14 through a bottom outlet 24 and is sub-cooled by passage through a further heat exchanger 26. The resulting sub-cooled methane-enriched liquid stream flows through a throttling valve 28 and is introduced into an intermediate mass exchange region of the lower pressure rectification column 16. In addition, a liquid stream comprising methane and nitrogen is withdrawn from an intermediate mass exchange region of the higher pressure rectification column 14 through an outlet 30, is sub-cooled by passage through the further heat exchanger 26, is passed through a throttling valve 32 and is introduced into a second intermediate mass exchange region of the lower pressure rectification column 16 located above the first intermediate mass exchange region.

The streams comprising methane and nitrogen are separated in the lower pressure rectification column 16 in order to form a top nitrogen vapour fraction and a bottom product liquid methane fraction. A stream of the bottom fraction is withdrawn through an outlet 40 from the lower pressure rectification column 16 and is raised in pressure by operation of a pump 42. The resulting pressurised product liquid methane stream is passed through the further heat exchanger 26 countercurrently to the streams being sub-cooled therein. The pressurisation of the product liquid methane stream has the effect of raising its pressure above its saturation pressure. Thus, in effect, the pressurised liquid methane product stream is in sub-cooled state as it enters the further heat exchanger 26. It is warmed in the further heat exchanger 26 to remove the sub-cooling. Preferably, no vaporisation of the liquid methane product stream takes place in the further heat exchanger 26. The warmed liquid methane product stream passes from the heat exchanger 26 through the main heat exchanger 4 from its cold end 8 to its warm end 6. It is vaporised as it passes through the main heat exchanger 4. The vaporised methane product is compressed to a desired product delivery pressure in a product compressor 60.

Reflux for the higher pressure rectification column 14 and the lower pressure rectification column 16 is formed by taking nitrogen vapour from the top of the higher pressure rectification column 14 and condensing it in the condensing passages of the condenser-reboiler 18. A part of the resulting condensate is returned to the higher pressure rectification column 14 as reflux. The remainder is sub-cooled by passage through the further heat exchanger 26 and is passed through a throttling valve 44 into the top of the lower pressure rectification column 16 and therefore provides liquid reflux for that column.

A nitrogen vapour stream is withdrawn from the top of the lower pressure rectification column 16 through an outlet 46, and warmed by passage through the further heat exchanger 26. The resulting warmed nitrogen stream is further warmed to approximately ambient temperature by passage through the main heat exchanger 4 from its cold end 8 to its warm end 6. The warmed nitrogen flow is divided into three sub-streams. One sub-stream is compressed in a recycle compressor 48 having a plurality of stages. A second sub-stream of the warmed nitrogen from the main heat exchanger 4 is employed in the regeneration of the adsorbent beds in the purification unit 2. A third sub-stream of the nitrogen is vented to atmosphere through a vent pipeline 50 as a waste stream. The relative size of the recycle stream is determined by the position of an adjustable flow control valve 52 on the inlet side of the recycle compressor 48.

The recycle gas flow entering the compressor 48 is divided into two parts. One stream passes through all the stages of the compressor and flows through the main heat exchanger 4 from its warm end 6 to its cold end 8. The resulting cooled stream of nitrogen is returned to an upper region of the higher pressure rectification column 14 through a throttling valve 54. The nitrogen is typically compressed to a supercritical pressure in the recycle compressor 48 and is cooled in the main heat exchanger 4 to a temperature sufficiently low for it to be liquefied by expansion through the throttling valve 54. The flow of this part of the recycle gas through the main heat exchanger 4 helps to match the composite temperature—enthalpy profile of the streams being cooled in the main heat exchanger 4 more closely to that of the streams being warmed therein.

An intermediate pressure stream is also withdrawn from the compressor 48 and is cooled by passage through the main heat exchanger 4 from its warm end 6 to its cold end 8. The intermediate pressure gas remains in gaseous state as it passes through the main heat exchanger 4 from its warm end 6 to its cold end 8. The intermediate pressure nitrogen is introduced into an upper region of the higher pressure rectification column 14 through an inlet 56. The intermediate pressure is therefore chosen to be essentially the operating pressure of the higher pressure rectification column 14. In an alternative arrangement, this intermediate pressure stream can also be introduced directly to the condenser-reboiler 18 (not shown in the Figure), with the resulting condensate being returned to the higher pressure rectification column 14 as reflux.

The part of the recycle gas that flows from the lower pressure rectification column 16 to the higher pressure rectification column 14 via the inlet 56 performs a heat pumping duty which enhances the production of liquid reflux for the rectification columns 14 and 16.

Initially, the purified feed gas stream typically contains about 95 mole percent of methane and 5 mole percent of nitrogen. The lower pressure rectification column 16 is operated at a pressure at its bottom of about 1.9 bar absolute. This sets the temperature at which the bottom fraction in the lower pressure rectification column boils. This temperature is one or two degrees Kelvin lower than the temperature at which the nitrogen top fraction separated in the higher pressure rectification column 14 is condensed in the condensing passages of the condenser-reboiler 18. As a result, the pressure in the lower pressure rectification column 16 sets the condensing pressure in the condenser-reboiler 18 and hence the operating pressure at the top of the higher pressure rectification column 14. When the pressure at the bottom of the lower pressure rectification column 16 is in order of 1.3 bar absolute, the operating pressure at the top of the higher pressure rectification column is in the order of 17 bar. Increasing the pressure at the bottom of the lower pressure rectification column 16 has the effect of producing a resultant increase in the operating pressure at the top of the higher pressure rectification column 14.

The pressure in the lower pressure rectification column 16 controlled by a back pressure regulating valve 58 in the outlet 46 for nitrogen from the lower pressure rectification column 16. The back pressure regulating valve 58 in controlling the pressure in the lower pressure rectification column 16 effectively controls the pressure at the top of the higher pressure rectification column 14. At first, the back pressure regulating valve 54 is typically arranged to be in a fully open or non-regulating position.

Methane is considerably less volatile than nitrogen. The initial feed gas composition is therefore relatively easy to liquefy as it contains a preponderance of methane. Typically, with a feed pressure of 40 bar absolute and a higher pressure rectification column 14 operating pressure of about 22 bar absolute, in the order of 75% by volume or more of the feed gas can be liquefied. The liquefaction of such a high proportion of the feed gas stream substantially reduces the vapour loading on the higher pressure rectification column 14 in comparison with what it would be if none of the feed gas stream were liquefied.

In a typical enhanced oil recovery or enhanced gas recovery operation, the proportion of nitrogen in the feed gas mixture gradually increases over the operating life of the well from about 5 mole percent to 60 mole percent. As the proportion of nitrogen increases in the feed gas mixture, it becomes more difficult to liquefy and hence the proportion of liquid in the fluid exiting the valve 23 gradually decreases. This has the effect of increasing the vapour loading on the higher pressure rectification column 14 even though the volumetric flow rate of the feed gas mixture remains unaltered.

It is customary to design a distillation column so that at maximum specified vapour loading it operates quite close to its flood point, say, at 80 to 90% of flood. The increase in the vapour loading that would take place as the mole percentage of nitrogen in the feed gas mixture increases from 5 to 60% is well in excess of that which would cause the column 14 to flood were its diameter to be selected such as to cause it to operate close to the flood point when the nitrogen mole percentage is at the bottom of its range. The effect of increasing nitrogen mole fraction in the feed gas can to some extent be mitigated by initially operating the higher pressure rectification column 14 at a lower vapour loading than 80% of flood and thereby increase the hydraulic operating range of the column.

The ability to turn down a liquid-vapour contact column depends on the choice of column internals to effect mass exchange between ascending vapour and descending vapour. In general, structured packing offers a greater degree of turndown than conventional liquid-vapour contact trays, be they of the bubble cap or sieve type. Accordingly, if structured packing is employed in the higher pressure rectification column 14, this enables it to be operated with a vapour loading of, say, about 50% of the flood point when the initial nitrogen mole fraction in the natural gas is 0.1. Even so, since the vapour loading is likely to increase more than twofold during the lifetime of the enhanced oil recovery or enhanced gas recovery operation, this measure of itself is unlikely to be entirely satisfactory. Further, it may be economically disadvantageous to build a column 14 which is initially considerably oversized if it is to be operated for several years at substantially less than an optimum vapour loading.

The method and apparatus according to the invention enable this problem to be mitigated by making use of the back pressure regulating valve 58 to control the pressure in the lower pressure rectification column 16 and hence the pressure in the higher pressure rectification column 14 so as to compensate for increasing nitrogen mole fraction in the higher pressure rectification column 14. In one arrangement the mole fraction of methane in the feed gas stream (either upstream or downstream of the purification unit), the mole fraction of methane in the product stream withdrawn from the outlet 40, and the flow rate of the product stream are all monitored and the percentage recovery of methane automatically calculated by appropriate process control software. The arrangement is such that the automatically calculated value of the methane recovery is used to control the setting of the back pressure regulating valve 58. In one embodiment, a control means is connected to the back pressure regulating valve 58 for maintaining a constant percentage recovery of methane in the product gas. The control means may, for example, comprise a controller and associated software known to one skilled in the art.

For example, the control may be arranged to raise the pressure in the lower pressure rectification column 16 and hence the higher pressure rectification column 14 if the recovery of methane instantaneously falls below 98.5% and the pressure drop in the higher pressure rectification column rises. A fall in product methane recovery could be caused by the vapour loading of the higher pressure rectification column rising to a level too close to the flood point, thereby causing the degree of separation in the higher pressure rectification column 14 to be reduced with the result that the impurity level in the product streams formed in the lower pressure rectification column 16 is increased. Increasing the pressure in the lower pressure rectification column 16 by resetting of the valve 58 increases the pressure in the higher pressure rectification column 14 thus reducing the vapour loading.

There is, however, another effect of an increasing mole fraction of nitrogen in the feed gas which, unlike its effect on the vapour loading of the column 14, favors high recovery of methane product. This effect is that with increasing nitrogen mole fraction there is an increased flow of vapour from the top of the column 14 into the condensing passages of the condenser-reboiler 18. Accordingly, more reflux is provided for the double rectification column. This makes it easier to separate the methane product. Under these conditions, the amount of nitrogen that is recycled from the lower pressure rectification column 16 to the higher pressure rectification column 14 can be reduced to keep down the power consumption of the recycle compressor. Such an adjustment can be made by changing the setting of the valve 52. The methane recovery may be used to control the valve 52 analogously to the valve 58. The operator of the plant therefore has two parameters to employ in controlling the process, namely the size of the flow through the valve 52 and the pressure at the top of the lower pressure rectification column 16.

It is preferred that the rate of recycle of nitrogen from the lower pressure column 16 to the higher pressure column 14 be at a maximum when the mole fraction of nitrogen in the feed gas stream is at a minimum. Provided that so doing does not move the higher pressure rectification column 14 too close to flood for product recovery to be maintained, it is normally preferred that the rate of recycle of nitrogen be progressively reduced as the mole fraction of nitrogen in the feed gas stream is increased. This is so as to minimise the power consumption of the method and apparatus according to the invention. One exception is if power is available particularly cheaply at the site where the method according to the invention is operated. It can then be advantageous to operate the higher pressure column 14 at a higher pressure, thus making separation more energy intensive therein, and recycle more nitrogen from the lower pressure column 16 to the higher pressure column 14 than would otherwise be necessary.

Typically, however, increasing the operating pressure of the rectification column 14 and 16 by resetting the valve 58 can with advantage be deferred until recycle of nitrogen has been reduced to a minimum. Typically, once the mole fraction of nitrogen in the feed gas has reached, say, 30% by volume, the passage of nitrogen through the inlet 56 is halted. It is still at such feed compositions desirable to continue to pass liquid nitrogen into the top of the higher pressure rectification column 14 via the expansion valve 54 so as to maintain a good match in the heat exchanger of the temperature—enthalpy profile of the streams being warmed with those being cooled. Accordingly, even if the inlet 56 is closed, it is preferred to maintain a sufficient flow of recycle gas through the recycle compressor to enable liquid to pass from the expansion valve 54 to the higher pressure rectification column 14 at the requisite rate.

The higher pressure rectification column 14 cannot of course be operated at critical pressure or above. There is therefore a ceiling on the range of operating pressure for this column. Thus, it is not desirable to increase the operating pressure of the higher pressure rectification column 14 much above about 29 bar absolute. Accordingly, we prefer to ensure that the operating pressure of the lower pressure rectification column 16 does not exceed about 3.5 bar absolute at its top.

Even if operation of the higher pressure rectification is started at a low vapour loading, say, one from one half to three quarters of that at flood point, the final nitrogen mole fraction in the feed gas may be so high that it becomes impossible to maintain a methane recovery of 98.5% or more over the full operating life of the method and apparatus according to the invention. If a drop in the methane purity towards the end of the operating life of the well or reservoir from which the feed gas is obtained is not tolerable, there is one other measure that can be adopted. This measure is to use two double rectification columns 12 in parallel with one another which share a common main heat exchanger 4 and a common sub-cooling heat exchanger 26. Typically, only one of the double columns 12 is employed for the full operating life of the well or reservoir and the other double column 12 is brought into use only towards the end of this operating life. If desired, both double columns may be installed together or one can be retro-fitted to the other. The use of such parallel double columns is described in and is the subject of a further patent application by this applicant which claims convention priority from GB patent application No. 0116977.0.

The method and apparatus according to the invention make it possible to select the size and the power consumption of a nitrogen rejection plant according to prevailing economic circumstances.

Various changes and modifications may be made to the method and apparatus according to the invention. For example, the recycle nitrogen flow, or some of it, can pass through a discrete heat exchanger separate from the main heat exchanger 4.

What is claimed is:

1. A method of rejecting nitrogen from a feed gas stream comprising methane and nitrogen so as to form a methane product, the mole fraction of nitrogen in the feed gas increasing over a period of time, the method comprising cooling the feed gas stream in a main heat exchanger, rectifying the cooled feed gas stream in a double rectification column comprising a higher pressure rectification column, a lower pressure rectification column, and a condenser-reboiler placing the higher pressure rectification column in heat exchange relationship with the lower pressure rectification column, expanding at least part of the feed gas stream into the higher pressure rectification column, partially liquefying the feed gas stream upstream of the double rectification column, and periodically increasing the operating pressure of the lower pressure rectification column in response to increases in the mole fraction of nitrogen in the feed gas stream.

2. The method according to claim 1, wherein a first flow of gas is passed as a first recycle gas flow from the lower pressure rectification column to the higher pressure rectification column.

3. The method according to claim 2, wherein the first recycle gas flow is compressed, is cooled in the main heat exchanger, is liquefied in the condenser-reboiler, and is introduced into the higher pressure rectification column.

4. The method according to claim 2, wherein a product methane stream is withdrawn in liquid state from the lower pressure rectification column, is raised in pressure, and is vaporised at least in part in the main heat exchanger.

5. The method according to claim 2, wherein a second recycle gas flow is taken from the lower pressure rectification column, is compressed, is cooled in the main heat exchanger, and is introduced at least partly in liquid state into the top of the higher pressure rectification column.

6. The method according to claim 2, wherein a second recycle gas flow is taken from the lower pressure rectification column, is compressed, is cooled in the main heat exchanger, and is introduced at least partly in liquid state into the top of the higher pressure rectification column and the second recycle gas flow is compressed to a higher pressure than the first recycle gas flow.

7. The method according to claim 2, wherein a second recycle gas flow is taken from the lower pressure rectification column, is compressed, is cooled in the main heat exchanger, and is introduced at least partly in liquid state into the top of the higher pressure rectification column, and the first and second recycle gas flows are compressed in a plural stage compressor, the second recycle flow being taken from a stage of the compressor downstream of a stage from which the first recycle flow is taken.

8. The method according to claim 2, wherein the first recycle gas flow is compressed before being passed to the higher pressure rectification column, and a vent stream is taken from the first recycle gas flow upstream of its compression and is vented.

9. The method according to claim 1, wherein the pressure in the lower pressure rectification column is adjusted so as to maintain a constant percentage recovery of methane in the product gas.

10. The method according to claim 1, wherein all the bottom fraction obtained in the higher pressure rectification column is withdrawn therefrom and is sent to the low pressure rectification column.

11. Apparatus for rejecting nitrogen from a feed gas stream comprising methane and nitrogen so as to form a methane product, the apparatus comprising a main heat exchanger for cooling the feed gas stream, a double rectification column for rectifying the feed gas stream comprising a higher pressure rectification column, a lower pressure rectification column, and a condenser-reboiler placing the higher pressure rectification column in heat exchange relationship with the lower pressure rectification column, and an expansion device downstream of the main heat exchanger communicating with the higher pressure rectification column, the expansion device being arranged for introducing a part of the feed gas stream into the higher pressure rectification column in liquid state, wherein there is a back pressure regulating valve associated with the lower pressure rectification column which is operable to increase the pressure in the lower pressure rectification column.

12. The apparatus according to claim 11, wherein the back pressure regulating valve is able to be controlled so as to maintain a constant percentage recovery of methane in the product gas.

* * * * *